United States Patent [19]

Mahmud et al.

[11] Patent Number: 5,916,934
[45] Date of Patent: Jun. 29, 1999

[54] ELASTOMERIC COMPOUNDS INCORPORATING PARTIALLY COATED CARBON BLACKS

[75] Inventors: Khaled Mahmud, Tyngsboro; Meng-Jiao Wang, Lexington; Steven R. Reznek, Concord; James A. Belmont, Acton, all of Mass.

[73] Assignee: Cabot Corporation, Boston, Mass.

[21] Appl. No.: 08/750,016

[22] PCT Filed: May 21, 1996

[86] PCT No.: PCT/US96/07309

§ 371 Date: Feb. 25, 1997

§ 102(e) Date: Feb. 25, 1997

[87] PCT Pub. No.: WO96/37546

PCT Pub. Date: Nov. 28, 1996

Related U.S. Application Data

[63] Continuation-in-part of application No. 08/446,140, May 22, 1995, abandoned, and a continuation-in-part of application No. 08/528,896, Sep. 15, 1995, abandoned.

[51] Int. Cl.⁶ ..................................................... C08K 9/04
[52] U.S. Cl. ............................................................. 523/215
[58] Field of Search ............................................. 523/215

[56] References Cited

U.S. PATENT DOCUMENTS

| | | | |
|---|---|---|---|
| T860,001 | 3/1969 | Gessler | 524/495 |
| 1,999,573 | 4/1935 | Odell | 134/60 |
| 2,121,535 | 6/1938 | Amon | 134/58 |
| 2,156,591 | 5/1939 | Jacobson | 196/50 |
| 2,375,795 | 5/1945 | Krejci | 23/209.8 |
| 2,502,254 | 3/1950 | Glassman | 106/289 |
| 2,514,236 | 7/1950 | Glassman | 106/289 |
| 2,564,700 | 8/1951 | Krejci | 23/209.4 |
| 2,625,492 | 1/1953 | Young | 106/303 |
| 2,632,713 | 3/1953 | Krejci | 106/307 |
| 2,793,100 | 5/1957 | Weihe | 23/209.1 |
| 2,833,736 | 5/1958 | Glaser | 260/29.6 |
| 2,867,540 | 1/1959 | Harris | 106/307 |
| 2,891,595 | 6/1959 | Kuntz et al. | 152/330 |
| 3,011,902 | 12/1961 | Jordon | 106/307 |
| 3,025,259 | 3/1962 | Wason et al. | 260/41.5 |
| 3,043,708 | 7/1962 | Watson et al. | 106/307 |
| 3,094,428 | 6/1963 | Hamilton et al. | 106/307 |
| 3,203,819 | 8/1965 | Steenken et al. | 260/41.5 |
| 3,317,458 | 5/1967 | Clas et al. | 106/307 |

(List continued on next page.)

FOREIGN PATENT DOCUMENTS

| | | |
|---|---|---|
| 0 006 190 A1 | 1/1980 | European Pat. Off. . |
| 272127 | 6/1988 | European Pat. Off. . |
| 0 411 160 A1 | 2/1991 | European Pat. Off. . |
| 433229 | 6/1991 | European Pat. Off. . |
| 0 441 987 A2 | 8/1991 | European Pat. Off. . |
| 0 501 227 A1 | 9/1992 | European Pat. Off. . |
| 410152 | 2/1994 | European Pat. Off. . |
| 636591 | 2/1995 | European Pat. Off. . |
| 0 641 823 A1 | 3/1995 | European Pat. Off. . |
| 0 646 621 A1 | 4/1995 | European Pat. Off. . |
| 0 711 805 A1 | 5/1996 | European Pat. Off. . |
| 2564489 | of 0000 | France . |
| 1164786 | 4/1960 | France . |
| 1215895 | 4/1960 | France . |
| E 72775 | 4/1960 | France . |

(List continued on next page.)

OTHER PUBLICATIONS

PCT Search Report PCT/US 96/07310, mailed Jan. 14, 1997.
Derwent Abstract, AN No. 80–03330C, "Sulphonated Carbon Pigment Production by Treating Technical Grade Carbon with Hot Aqueous Acid," SU,A,659, 523, Apr. 1979.
Derwent Abstract, AN No. 82–28019E, "Penetrating Flexographic Print Ink Based Polyacrylic Resin," Oct. 17, 1979, SU,A 834062.
Derwent Abstract, AN No. 86–335147, "Wear Resistant Rubber Composition for Tire Tread Rubber," Apr. 30, 1985, JPA 61–250042, Nov. 198.
Derwent Abstract WPI Acc No. 94–031974/04, Japanese Patent Application No. 92145679, 1992.
Derwent Abstract WPI Acc No. 94–072121/09, Japanese Patent Application No. 9295517, 1992.
Derwent Abstract WPI Acc No. 94–121502/15, Japanese Patent Application No. 92241473, 1992.
Derwent Abstract WPI Acc No. 94–124167/15, Japanese Patent Application No. 9133147, 1991.
Derwent Abstract, AN No. 95–183086, "Tire Treated Rubber Composition," Oct. 21, 1993, JPA 07102116.
Derwent Abstract, AN No. 94–189154, "Ink for Writing Implements," May 10, 1994, JPA 61–28517A.
Patent Abstracts of Japan Publication No. JP7102116, "Rubber Composition for Tire Tread," Apr. 18, 1995.
Moschopedis, et al., "The Reaction of Diazonium Salts with Humic Acids and Coals: Evidence for Activated Methylene Bridges in Coals and Humic Acids," *Fuel*, vol. 43, No. 4, pp. 289–298, 1964.
Roberts et al., *Basic Principles of Organic Chemistry*, Second Edition, W.A. Benjamin, Inc., Pub., p. 1080.
Allen, "Thermal Ink Jet Printing Trends and Advances," BIS Ink Jet Printing Conference, Oct. 10–12, 1994, Monterey, California.
Schneider, "Continuous Ink Jet," BIS Ink Jet Printing Conference, Oct. 10–12, 1994, Monterey, California.
Major, "Formulating the Future of Automative Coatings," *Modern Paint and Coatings*, Jul. 1993.
Greenfield, "Fewer Formulation Options Lead to Emphasis on Familiar," *Modern Paint and Coatings*, Jul. 1992.

(List continued on next page.)

*Primary Examiner*—Paul R. Michl

[57] ABSTRACT

Disclosed are elastomeric compounds including an elastomer, a silica coated carbon black, and optionally including a coupling agent. Elastomeric compounds incorporating an elastomer and an oxidized, partially coated carbon black are also disclosed. Also disclosed are silica coated carbon black/elastomeric formulations using a variety of elastomers useful in a variety of product applications.

33 Claims, No Drawings

U.S. PATENT DOCUMENTS

| | | | |
|---|---|---|---|
| 3,335,020 | 8/1967 | Aboytes et al. | 106/307 |
| 3,390,006 | 6/1968 | Takewell et al. | 106/288 |
| 3,479,300 | 11/1969 | Rivin et al. | 252/430 |
| 3,528,840 | 9/1970 | Aboytes | 106/307 |
| 3,607,813 | 9/1971 | Purcell et al. | 260/29.6 |
| 3,622,650 | 11/1971 | Berstein et al. | 260/763 |
| 3,660,132 | 5/1972 | Illigen et al. | 106/307 |
| 3,663,285 | 5/1972 | Graf et al. | 106/308 |
| 3,674,670 | 7/1972 | Erikson et al. | 204/181 |
| 3,686,111 | 8/1972 | Makhlouf et al. | 260/31.2 |
| 3,689,452 | 9/1972 | Burke, Jr. | 260/33.6 |
| 3,716,513 | 2/1973 | Burke, Jr. | 260/33.6 |
| 3,846,141 | 11/1974 | Ostergren et al. | 106/22 |
| 3,873,489 | 3/1975 | Thurn et al. | 260/33.6 |
| 3,876,603 | 4/1975 | Makhlouf | 260/31.2 |
| 3,997,356 | 12/1976 | Thurn et al. | 106/288 |
| 4,003,751 | 1/1977 | Carder | 106/20 |
| 4,006,031 | 2/1977 | Ferch et al. | 106/307 |
| 4,014,833 | 3/1977 | Story | 260/29.2 |
| 4,014,844 | 3/1977 | Vidal et al. | 260/31.2 |
| 4,061,830 | 12/1977 | Greenberg | 428/469 |
| 4,071,496 | 1/1978 | Kraus et al. | 260/42.36 |
| 4,074,035 | 2/1978 | Powers et al. | 526/185 |
| 4,108,679 | 8/1978 | Szczepanik et al. | 106/307 |
| 4,176,361 | 11/1979 | Kawada et al. | 346/1.1 |
| 4,204,871 | 5/1980 | Johnson et al. | 106/20 |
| 4,204,876 | 5/1980 | Bowden | 106/90 |
| 4,211,578 | 7/1980 | Scott, IV | 106/307 |
| 4,221,693 | 9/1980 | Getson | 523/213 |
| 4,229,333 | 10/1980 | Wolff et al. | 260/23.7 |
| 4,290,072 | 9/1981 | Mansukhani | 346/1.1 |
| 4,293,394 | 10/1981 | Darlington et al. | 204/98 |
| 4,297,145 | 10/1981 | Wolff et al. | 106/308 |
| 4,308,061 | 12/1981 | Iwahashi et al. | 106/22 |
| 4,328,041 | 5/1982 | Wilson | 106/308 |
| 4,360,627 | 11/1982 | Okado et al. | 524/496 |
| 4,442,256 | 4/1984 | Miller et al. | 524/539 |
| 4,451,597 | 5/1984 | Victorius | 524/39 |
| 4,468,496 | 8/1984 | Takeuchi et al. | 525/333 |
| 4,476,270 | 10/1984 | Brasen et al. | 524/364 |
| 4,478,905 | 10/1984 | Neely, Jr. | 428/324 |
| 4,503,174 | 3/1985 | Vasta | 523/439 |
| 4,503,175 | 3/1985 | Houze et al. | 524/39 |
| 4,517,335 | 5/1985 | Wolff et al. | 524/552 |
| 4,525,521 | 6/1985 | DenHartog et al. | 524/517 |
| 4,525,570 | 6/1985 | Blum et al. | 528/75 |
| 4,530,961 | 7/1985 | Nguyen et al. | 524/832 |
| 4,544,687 | 10/1985 | Schupp et al. | 523/414 |
| 4,555,535 | 11/1985 | Bednarek et al. | 524/40 |
| 4,556,427 | 12/1985 | Lewis | 106/20 |
| 4,590,052 | 5/1986 | Chevallier et al. | 423/335 |
| 4,597,794 | 7/1986 | Ohta et al. | 106/20 |
| 4,605,542 | 8/1986 | Harada | 423/345 |
| 4,605,596 | 8/1986 | Fry | 428/423.3 |
| 4,620,993 | 11/1986 | Suss et al. | 427/407.1 |
| 4,620,994 | 11/1986 | Suss et al. | 427/407.1 |
| 4,650,718 | 3/1987 | Simpson et al. | 428/413 |
| 4,659,770 | 4/1987 | Vasta | 524/553 |
| 4,665,128 | 5/1987 | Cluff et al. | 525/131 |
| 4,670,059 | 6/1987 | Hackleman et al. | 106/307 |
| 4,680,204 | 7/1987 | Das et al. | 427/407.1 |
| 4,681,811 | 7/1987 | Simpson et al. | 428/413 |
| 4,692,481 | 9/1987 | Kelly | 523/219 |
| 4,710,543 | 12/1987 | Chattha et al. | 525/161 |
| 4,713,427 | 12/1987 | Chattha et al. | 525/510 |
| 4,719,132 | 1/1988 | Porter, Jr. | 427/409 |
| 4,727,100 | 2/1988 | Vasta | 524/40 |
| 4,741,780 | 5/1988 | Atkinson | 106/308 |
| 4,752,532 | 6/1988 | Starka | 428/482 |
| 4,764,430 | 8/1988 | Blackburn et al. | 428/413 |
| 4,770,706 | 9/1988 | Pietsch | 106/24 |
| 4,789,400 | 12/1988 | Solodar et al. | 106/22 |
| 4,798,745 | 1/1989 | Martz et al. | 27/407.1 |
| 4,798,746 | 1/1989 | Claar et al. | 427/407.1 |
| 4,808,656 | 2/1989 | Kania et al. | 524/512 |
| 4,820,751 | 4/1989 | Takeshita | 523/215 |
| 4,822,844 | 4/1989 | Kawakami et al. | 524/496 |
| 4,824,900 | 4/1989 | Sakurai | 524/495 |
| 4,840,674 | 6/1989 | Schwarz | 106/22 |
| 4,853,037 | 8/1989 | Johnson et al. | 106/22 |
| 4,866,131 | 9/1989 | Fujimaki et al. | 525/119 |
| 4,883,838 | 11/1989 | Jung et al. | 525/237 |
| 4,894,420 | 1/1990 | Scriver | 525/237 |
| 4,908,397 | 3/1990 | Barsotti et al. | 523/400 |
| 4,914,148 | 4/1990 | Hille et al. | 524/507 |
| 4,927,868 | 5/1990 | Schimmel et al. | 523/439 |
| 4,975,474 | 12/1990 | Barsotti et al. | 523/400 |
| 4,994,520 | 2/1991 | Mori et al. | 524/547 |
| 5,008,223 | 4/1991 | Speer et al. | 106/450 |
| 5,008,335 | 4/1991 | Pettit, Jr. | 525/111 |
| 5,017,435 | 5/1991 | Barsotti et al. | 428/502 |
| 5,026,755 | 6/1991 | Kveglis et al. | 524/389 |
| 5,051,464 | 9/1991 | Johnson et al. | 524/555 |
| 5,064,719 | 11/1991 | DenHartog et al. | 428/411.1 |
| 5,066,733 | 11/1991 | Martz et al. | 525/455 |
| 5,076,843 | 12/1991 | Acitelli et al. | 106/22 |
| 5,093,391 | 3/1992 | Barsotti et al. | 523/400 |
| 5,093,407 | 3/1992 | Komai et al. | 524/495 |
| 5,100,470 | 3/1992 | Hindagolla et al. | 106/22 |
| 5,106,417 | 4/1992 | Hauser et al. | 106/20 |
| 5,109,055 | 4/1992 | Nagasaki et al. | 524/571 |
| 5,114,477 | 5/1992 | Mort et al. | 106/20 |
| 5,122,552 | 6/1992 | Johnson | 523/454 |
| 5,130,004 | 7/1992 | Johnson et al. | 204/181.7 |
| 5,130,363 | 7/1992 | Scholl et al. | 524/392 |
| 5,141,556 | 8/1992 | Matrick | 106/20 |
| 5,152,801 | 10/1992 | Altermatt et al. | 8/436 |
| 5,159,009 | 10/1992 | Wolff et al. | 524/495 |
| 5,162,409 | 11/1992 | Mroczkowski | 524/262 |
| 5,168,106 | 12/1992 | Babcock et al. | 524/495 |
| 5,173,111 | 12/1992 | Krishnan et al. | 106/20 |
| 5,179,191 | 1/1993 | Jung et al. | 528/272 |
| 5,182,355 | 1/1993 | Martz et al. | 528/75 |
| 5,184,148 | 2/1993 | Suga et al. | 346/1.1 |
| 5,190,582 | 3/1993 | Shinozuka et al. | 106/20 |
| 5,200,164 | 4/1993 | Medalia et al. | 423/265 |
| 5,204,404 | 4/1993 | Werner, Jr. et al. | 524/501 |
| 5,206,295 | 4/1993 | Harper et al. | 525/207 |
| 5,221,581 | 6/1993 | Palmer et al. | 428/425.8 |
| 5,227,425 | 7/1993 | Rauline | 524/493 |
| 5,229,452 | 7/1993 | Green et al. | 524/415 |
| 5,232,974 | 8/1993 | Branan, Jr. et al. | 524/495 |
| 5,236,992 | 8/1993 | Bush | 524/495 |
| 5,242,751 | 9/1993 | Hartman | 428/324 |
| 5,266,361 | 11/1993 | Schwarte et al. | 427/407.1 |
| 5,266,406 | 11/1993 | DenHartog et al. | 428/423.1 |
| 5,276,097 | 1/1994 | Hoffmann et al. | 525/167 |
| 5,281,261 | 1/1994 | Lin | 106/20 |
| 5,286,286 | 2/1994 | Winnik et al. | 524/496 |
| 5,286,291 | 2/1994 | Bernhardt et al. | 106/20 |
| 5,288,788 | 2/1994 | Shieh et al. | 524/496 |
| 5,290,848 | 3/1994 | Palmer et al. | 524/517 |
| 5,294,253 | 3/1994 | Carlson et al. | 106/475 |
| 5,294,585 | 3/1994 | Moreau et al. | 502/413 |
| 5,302,197 | 4/1994 | Wickramanayke et al. | 106/22 |
| 5,310,778 | 5/1994 | Shor et al. | 524/556 |
| 5,314,945 | 5/1994 | Nickle et al. | 525/507 |
| 5,314,953 | 5/1994 | Corcoran et al. | 525/123 |
| 5,319,044 | 6/1994 | Jung et al. | 526/279 |
| 5,320,738 | 6/1994 | Kaufman | 205/317 |
| 5,324,790 | 6/1994 | Manring | 525/329.9 |
| 5,328,949 | 7/1994 | Sandstrom | 524/262 |

| | | | |
|---|---|---|---|
| 5,334,650 | 8/1994 | Serdiuk et al. | 524/591 |
| 5,336,716 | 8/1994 | Kappes et al. | 525/23 |
| 5,336,730 | 8/1994 | Sandstrom | 525/332.6 |
| 5,336,753 | 8/1994 | Jung et al. | 528/335 |
| 5,352,289 | 10/1994 | Weaver et al. | 106/476 |
| 5,356,973 | 10/1994 | Taljan et al. | 524/314 |
| 5,366,828 | 11/1994 | Struthers | 429/101 |
| 5,401,313 | 3/1995 | Supplee et al. | 106/712 |
| 5,401,789 | 3/1995 | Wolf et al. | 524/288 |
| 5,411,577 | 5/1995 | Moreau et al. | 95/96 |
| 5,430,087 | 7/1995 | Carlson et al. | 534/885 |
| 5,554,739 | 9/1996 | Belmont | 523/215 |
| 5,559,169 | 9/1996 | Belmont | 523/215 |
| 5,571,311 | 11/1996 | Belmont et al. | 106/20 |
| 5,575,845 | 11/1996 | Belmont et al. | 106/20 |
| 5,622,557 | 4/1997 | Mahmud | 106/712 |
| 5,679,728 | 10/1997 | Kawazura | 523/215 |
| 5,707,432 | 1/1998 | Adams | 106/31.6 |
| 5,713,988 | 2/1998 | Belmont | 106/31.6 |

FOREIGN PATENT DOCUMENTS

| | | |
|---|---|---|
| 1224131 | 6/1960 | France . |
| 1230893 | 9/1960 | France . |
| 1331889 | 5/1963 | France . |
| 2477593 | 11/1981 | France . |
| 2607528 | 6/1988 | France . |
| 24 26 266 A1 | 12/1975 | Germany . |
| 3170748 | 7/1985 | Germany . |
| 35 02 494 A1 | 8/1985 | Germany . |
| 59/82467 | 5/1984 | Japan . |
| 01/275666 | 11/1989 | Japan . |
| 5-178604 | 7/1993 | Japan . |
| 05/271365 | 10/1993 | Japan . |
| 5339516 | 12/1993 | Japan . |
| 06/025572 | 2/1994 | Japan . |
| 6025572 | 2/1994 | Japan . |
| 6067421 | 3/1994 | Japan . |
| 6073235 | 3/1994 | Japan . |
| 7-30269 | 4/1995 | Japan . |
| 862018 | 3/1961 | United Kingdom . |
| 972626 | 8/1963 | United Kingdom . |
| 1139620 | 1/1969 | United Kingdom . |
| 1191872 | 5/1970 | United Kingdom . |
| 1213186 | 11/1970 | United Kingdom . |
| 1363428 | 8/1974 | United Kingdom . |
| 2044741 | 10/1980 | United Kingdom . |
| WO 91/15425 | 10/1991 | WIPO . |
| WO 92/13983 | 8/1992 | WIPO . |
| WO 96/18688 | 6/1996 | WIPO . |
| WO 96/18696 | 6/1996 | WIPO . |
| WO 96/37547 | 11/1996 | WIPO . |

OTHER PUBLICATIONS

Schrantz, "Regulations and Competition Push Technological Change," *Modern Paint and Coatings*, Jul. 1994.

"Regulations Focus Formulator Attention on Additives," *Modern Paint and Coatings*, Jul. 1994.

*The Printing Ink Manual*, Fifth Edition, R.H. Leach et al., Blueprint Press, Chapters 8, 9, and 10.

Tsubokawa, "Functionalization of Carbon Black by Surface Grafting of Polymers," *Polym. Sci.*, vol. 17, pp. 417–470, 1992.

Wolff et al., "The Influence of Modified Carbon Blacks on Viscoelastic Compound Properties," *Kautschuk & Gummi*, Kuststoffe 44, Jahrgang, Nr. Oct. 1991.

Bourdillon et al., "Immobilization of Glucose Oxidase on a Carbon Surface Derivatized by Electrochemical Reduction of Diazonium Salts," *J. Electroanal. Chem.*, vol. 336, pp. 113–123, 1992.

Ohkita et al., "The Reaction of Carbon Black Surface with 2,2–Diphenyl–1–Picrylhydrazyl," *Carbon*, vol. 10, No. 5, pp. 631–636, 1972.

Watson, "Chemical Aspects of Reinforcement," Compounding Research Department, Dunlop Research Center, Dunlop Rubber Co., pp. 987–999.

Garten et al., "Nature of Chemisorptive Mechanisms in Rubber Reinforcement," Commonwealth Scientific and Industrial Research Organ., Div. of Industrial Chem., Melbourne, Australia, pp. 596–609.

Donnet et al., "Chimie Superficielle et Sites Privilegies Des Charges Fines," Extrait de la Revue Generale du Caoutchoic, Jul. 1959.

*Ullmann's Encyclopedia of Industrial Chemistry*, Fifth Edition, vol. A–8, pp. 508–509, 1987.

Donnet et al., "Sur la Structure Aroxylique des Groupements Quinoniques et des Radicaux Libres Presentes en Surface des Noirs de Carbon," *Ref. Gen. Caoutchouc Plastiques*, vol. 42, No. 3, pp. 389–392, 1965 (with English Abstract).

Yamaguchi et al., "Novel Carbon Black/Rubber Coupling Agent," *Kautschuk & Gummi*, Kuntstoffe 42, Jahrgang, Nr. May 1989.

Studebaker et al., "Oxygen–Containing Groups on the Surface of Carbon Black," *Industrial and Engineering Chemistry*, vol. 48, No. 1, pp. 162–166, Jan. 1956.

Zoheidi et al., "Role of Oxygen Surface Groups in Catalysis of Hydrogasification of Carbon Black by Potassium Carbonate," *Carbon*, vol. 25, No. 6, pp. 808–819, 1987.

Scherrer, "Coloration of Ink Jet Inks," Presentation of BIS Ink Jet Printing Conference, Oct. 10–12, 1994, Monterey.

*Ink Jet Printing: 1994 Overview and Outlook*, Chapter 7.

*The Printing Ink Manual*, Fourth Edition, Chapter 2, Leach et al., Eds., 1988.

Andreottoia, *Ink Jet Ink Technology*, pp. 531–544.

Gregory, *High–Technology Applications of Organic Colorants*, Chapter 9, "Ink–Jet Printing," 1991.

PCT Search Report, PCT/US 95 16452, Apr. 17, 1996.

PCT Search Report, PCT/US 95/16195, Apr. 19, 1996.

PCT Search Report, PCT/US 95/16281, Apr. 26, 1996.

PCT Search Report, PCT/IB 95/01154, Apr. 29, 1996.

PCT Search Report, PCT/US 95/16453, May 15, 1996.

Chemical Abstract No. 113:116901, Nov. 6, 1989.

Chemical Abstract No. 120325954, Feb. 1, 1994.

RAPRA Abstract No. 432845, "Compound Heat Resistant Non–Black EPDM Rubber Compounding Report," Dec. 1990.

RAPRA Abstract No. 417612, "Review: Polymer–Filler Interactions in Rubber Reinforcement," Oct. 1990.

RAPRA Abstract No. 403202, "Organotitanate, Zirconate Effect on Elastomers," Jun. 1990.

RAPRA Abstract No. 394030, "Mechanical Properties of Natural Rubber/Grafted Cellulose Fibre Composites," 1990.

RAPRA Abstract No. 390600, "Application of Coupling Agents to Elastomers," 1989.

RAPRA Abstract No. 00388935, "Light Coulored Fillers in Polymers," Nov. 1989.

Dialog Abstract EMA No. 8602–C1–D–0297, "Carbon Black is Better With Silica," Oct. 1985.

RAPRA Abstract No. 00343229, "White and Black Fillers for Rubber Compounds," Dec. 1986.

RAPRA Abstract No. 00177481, "Ethylene–Propylene Rubbers," 1981.

RAPRA Abstract No. 00105623, "Putting Performance Into Thermosets with Titanium Coupling Agents," Oct. 1976.

RAPRA Abstract No. 00056893, "Applications for Silane Coupling Agents in the Automotive Industry," Oct. 1975.

RAPRA Abstract No. 00002608, "Ground Rice Hull Ash as a Filler for Rubber," Oct. 1974.

RAPRA Abstract No. 00000937, "Reduction of Heat Build–up in Mineral–Filled Elastomers Through the Use of Silane Coupling Agents," May 1973.

RAPRA Abstract No. 00105623, "Putting Performance into Thermosets With Titanium Coupling Agents," Oct. 1976.

Derwent Abstract, Japanese Patent Publication No. 80–73657, Mar. 19, 1996.

Derwent Abstract, WPI Acc No. 78–73373A/41, Japanese Patent Application No. 53–100190, 1978.

Derwent Abstract, WPI Acc No. 95–019436/03, Japanese Patent Application No. 63–06289, 1994.

Derwent Abstract, WPI Acc No. 92–369382/45, Japanese Patent Application No. 4–270199, 1992.

Derwent Abstract, WPI Acc No. 90–335599/45, DD No. 279537, 1990.

Derwent Abstract, WPI Acc No. 90–128540/17, Japanese Patent Application No. 2–077483, 1990.

Derwent Abstract, WPI Acc No. 88–261546/37, Japanese Patent Application No. 63–190800, 1988.

Derwent Abstract, WPI Acc No. 87–034097/05, Japanese Patent Application No. 61–291659, 1986.

Derwent Abstract, WPI Acc No. 88–052867/08, Japanese Patent Application No. 63–008442, 1988.

Chemical Abstract vol. 114, No. 14, No. 124715d (1990).

Chemical Abstract vol. 112, No. 18, No. 160248w, 1988.

Chemical Abstract vol. 110, No. 6, No. 48370n, 1986.

Chemical Abstract vol. 69, No. 18, No. 68396p, 1967.

Chemical Abstract vol. 94, No. 16, No. 122906m, 1980.

Chemical Abstract vol. 66, No. 24, No. 105491b, 1966.

Chemical Abstract vol. 67, No. 2, No. 3806m, 1966.

Chemical Abstract vol. 102, No. 4, No. 28447z, 1984.

Chemical Abstract vol. 100, No. 22, No. 176125s, 1983.

Chemical Abstract vol. 106, No. 28, No. 224473b, 1987.

Chemical Abstract vol. 94, No. 8, No. 48630y, 1980.

Chemcial Abstract vol. 88, No. 22, No. 161466p, 1978.

Chemical Abstract vol. 104, No. 12, No. 90590k, 1985.

Chemical Abstract vol. 105, No. 8, No. 61488y, 1985.

Ouyang et al., "Carbon Black Effects on Treadwear," Presented at a Meeting of the Rubber Division, American Chemical Society, Las Vegas, Nevada, May 29–Jun. 1, 1990.

Agostini, et al., "New Compound Technology," Goodyear Technical Center, Luxembourg.

Dialog Abstract of Japanese Application No. 4–362009, 1992.

Dialog Abstract of Japanese Application No. 4–276000, 1992.

Studebaker et al., "The Rubber Compound and its Composition," *Science and Technology of Rubber*, Academic Press, 1978, Chapter 9, pp. 367–375.

"Tires," Reprinted from *Encyclopedia of Polymer Science and Engineering*, vol. 16, Second Edition, 1969, pp. 834–861.

Tsubokawa et al., "Grafting Onto Carbon Black Having Few Functional Groups," Shikizai Kyokaisha, vol. 66, No. 5 (1993), Abstract Only.

J.B. Donnet et al., "Radical Reactions and Surface Chemistry of Carbon Black," Bull. Soc. Chim. 1960 (Abstract Only).

Concise Encyclopedia of Polymer Science and Engineering, Wiley, 1990, pp. 104–105.

Carbon (Carbon Black) Reprinted from Kirk–Othmer: Encyclopedia of Chemical Technology, vol. 4, Third Edition, pp. 631–643, 1978.

Delamar et al., J. Am. Chem. Soc. 1992, 114, 5883–5884.

Kang, "Water–Based Ink–Jet Ink," J. Imaging Science, vol. 35, No. 3, May/Jun., 1991, pp. 195–201.

U.S. Patent Application No. 08/356,462, Dec. 15, 1994.

U.S. Patent Application No. 08/356,459, Dec. 15, 1994.

U.S. Patent Application No. 08/356,460, Dec. 15, 1994.

U.S. Patent Application No. 08/356,653, Dec. 15, 1994.

U.S. Patent Application No. 08/356,664, Dec. 14, 1994.

U.S. Patent Application Serial No. 08/446,140, May 22, 1995.

U.S. Patent Application Serial No. 08/446,142, May 22, 1995.

U.S. Patent Application Serial No. 08/446,143, May 22, 1995.

U.S. Patent Application No. 08/572,526, Dec. 14, 1995.

U.S. Patent Application No. 08/572,336, Dec. 14, 1995.

U.S. Patent Application No. 08/572,545, Dec. 14, 1995.

ELASTOMERIC COMPOUNDS INCORPORATING PARTIALLY COATED CARBON BLACKS

This application is a Continuation-in-Part of U.S. patent application Nos. 08/446,140, filed May 22, 1995 now abandoned, and 08/528,896, filed Sep. 15, 1995 now abandoned, and is a National Phase Application of PCT/US96/07309, filed May 21, 1996.

TECHNICAL FIELD

The present invention relates to novel elastomeric compounds exhibiting improved hysteresis properties. More particularly, the invention relates to novel elastomeric compounds incorporating silica coated carbon blacks.

BACKGROUND ART

Carbon blacks are widely used as pigments, fillers and reinforcing agents in the compounding and preparation of rubber and other elastomeric compounds. Carbon blacks are particularly useful as reinforcing agents in the preparation of elastomeric compounds used in the manufacture of tires.

Carbon blacks are generally produced in a furnace-type reactor by pyrolyzing a hydrocarbon feedstock with hot combustion gases to produce combustion products containing particulate carbon black. Carbon black exists in the form of aggregates. The aggregates, in turn are formed of carbon black particles. However, carbon black particles do not generally exist independently of the carbon black aggregate. Carbon blacks are generally characterized on the basis of analytical properties, including, but not limited to particle size and specific surface area; aggregate size, shape, and distribution; and chemical and physical properties of the surface. The properties of carbon blacks are analytically determined by tests known to the art. For example, nitrogen adsorption surface area (measured by ASTM test procedure D3037-Method A) and cetyl-trimethyl ammonium bromide adsorption value (CTAB) (measured by ASTM test procedure D3765 [09.01]), are measures of specific surface area. Dibutylphthalate absorption of the crushed (CDBP) (measured by ASTM test procedure D3493-86) and uncrushed (DBP) carbon black (measured by ASTM test procedure D2414-93), relates to the aggregate structure. The bound rubber value relates to the surface activity of the carbon black. The properties of a given carbon black depend upon the conditions of manufacture and may be modified, e.g., by altering temperature, pressure, feedstock, residence time, quench temperature, throughput, and other parameters.

It is generally desirable in the production of tires to employ carbon black-containing compounds when constructing the tread and other portions of the tire. For example, a suitable tread compound will employ an elastomer compounded to provide high abrasion resistance and good hysteresis balance at different temperatures. A tire having high abrasion resistance is desirable because abrasion resistance is proportional to tire life. The physical properties of the carbon black directly influence the abrasion resistance and hysteresis of the tread compound. Generally, a carbon black with a high surface area and small particle size will impart a high abrasion resistance and high hysteresis to the tread compound. Carbon black loading also affects the abrasion resistance of the elastomeric compounds. Abrasion resistance increases with increased loading, at least to an optimum point, beyond which abrasion resistance actually decreases.

The hysteresis of an elastomeric compound relates to the energy dissipated under cyclic deformation. In other words, the hysteresis of an elastomeric composition relates to the difference between the energy applied to deform the elastomeric composition and the energy released as the elastomeric composition recovers to its initial undeformed state. Hysteresis is characterized by a loss tangent, tan δ, which is a ratio of the loss modulus to the storage modulus (that is, viscous modulus to elastic modulus). Tires made with a tire tread compound having a lower hysteresis measured at higher temperatures, such as 40° C. or higher, will have reduced rolling resistance, which in turn, results in reduced fuel consumption by the vehicle using the tire. At the same time, a tire tread with a higher hysteresis value measured at low temperature, such as 0° C. or lower, will result in a tire with high wet traction and skid resistance which will increase driving safety. Thus, a tire tread compound demonstrating low hysteresis at high temperatures and high hysteresis at low temperatures can be said to have a good hysteresis balance.

There are many other applications where it is useful to provide an elastomer exhibiting a good hysteresis balance but where the abrasion resistance is not an important factor. Such applications include but are not limited to tire components such as undertread, wedge compounds, sidewall, carcass, apex, bead filler and wire skim; engine mounts; and base compounds used in industrial drive and automotive belts.

Silica is also used as a reinforcing agent (or filler) for elastomers. However, using silica alone as a reinforcing agent for elastomer leads to poor performance compared to the results obtained with carbon black alone as the reinforcing agent. It is theorized that strong filler-filler interaction and poor filler-elastomer interaction accounts for the poor performance of silica. The silica-elastomer interaction can be improved by chemically bonding the two with a chemical coupling agent, such as bis (3-triethoxysilylpropyl) tetrasulfane, commercially available as Si-69 from Degussa AG, Germany. Coupling agents such as Si-69 create a chemical linkage between the elastomer and the silica, thereby coupling the silica to the elastomer.

When the silica is chemically coupled to the elastomer, certain performance characteristics of the resulting elastomeric composition are enhanced. When incorporated into vehicle tires, such elastomeric compounds provide improved hysteresis balance. However, elastomer compounds containing silica as the primary reinforcing agent exhibit low thermal conductivity, high electrical resistivity, high density and poor processibility.

When carbon black alone is used as a reinforcing agent in elastomeric compositions, it does not chemically couple to the elastomer but the carbon black surface provides many sites for interacting with the elastomer. While the use of a coupling agent with carbon black might provide some improvement in performance to an elastomeric composition, the improvement is not comparable to that obtained when using a coupling agent with silica.

It is an object of the present invention to provide novel elastomeric compounds exhibiting improved hysteresis balance. It is another object to provide an elastomeric compound incorporating silica coated carbon blacks. It is yet another object of the present invention to provide an elastomeric compound incorporating silica coated carbon blacks, wherein the carbon black may be efficiently coupled to the elastomer with a coupling agent. Such a carbon black may be employed for example, in tire compounds, industrial rubber products and other rubber goods. It is a further object of the present invention to provide silica coated carbon black/elastomeric formulations using a variety of elastomers useful in a variety of product applications. Other objects of the present invention will become apparent from the following description and claims.

DISCLOSURE OF THE INVENTION

The present invention is directed to an elastomeric compound including an elastomer and a silica coated carbon black, and optionally including a coupling agent. The silica coated carbon black imparts to the elastomer improved hysteresis compared to an uncoated carbon black. The invention is also directed to silica coated carbon black/elastomeric formulations using a variety of elastomers useful in a variety of product applications.

DETAILED DESCRIPTION OF THE INVENTION

Elastomeric compounds having desirable hysteresis and other properties may be obtained by compounding an elastomer with a silica coated carbon black.

The silica coated carbon blacks may be obtained by coating a silicon oxide compound onto at least a portion of the carbon black aggregate. Any carbon black may be used.

The carbon black may be fully or partially coated with a silicon oxide compound by a number of different methods. One such method is taught in Japanese (Kokai) patent application No. HEI 5(1993)-178604. To prepare the silica coated carbon black, an organo-silicate such as tetraethylorthosilicate, or a silane such as tetraethoxysilane, may be diluted with a solvent such as methanol to produce a silicon compound solution having a concentration of between about 1 and 20% by weight of the silicon compound. Another solution is made by adding 5–20% of a 28% aqueous ammonia solution to ethanol.

A carbon black is then slowly added to the ammonia solution, while continuously stirring the mixture. Simultaneously, the silicon compound solution is added dropwise to the ammonia solution. After up to several hours of this operation, the silica coated carbon black is extracted, filtered and dried.

A carbon black coated with silica, thus made, is expected to impart advantages over carbon black, silica, or mixtures thereof in an elastomer. Without being bound by theory, it is believed that such a silica coated carbon black would have more functional groups, specifically silanols, on its surface, allowing for greater interaction with a coupling agent, thereby improving hysteresis when compounded with an elastomer compared to uncoated carbon black. The silica coated carbon black is also expected to impart significant advantages over silica in an elastomer. Accordingly, less coupling agent would be required, resulting in reduced compounding costs.

Elastomeric compounds incorporating a silica coated carbon black as disclosed above may be additionally compounded with one or more coupling agents to further enhance the properties of the elastomeric compound. Coupling agents, as used herein, include, but are not limited to, compounds that are capable of coupling fillers such as carbon black or silica to an elastomer. Useful coupling agents include, but are not limited to, silane coupling agents such as bis(3-triethoxysilylpropyl)tetrasulfane (Si-69), 3-thiocyanatopropyl-triethoxy silane (Si-264, from Degussa AG), γ-mercaptopropyl-trimethoxy silane (A189, from Union Carbide Corp., Danbury, Conn.); zirconate coupling agents, such as zirconium dineoalkanolatodi(3-mercapto) propionato-O (NZ 66A, from Kenrich Petrochemicals, Inc., of Bayonne, N.J.); titanate coupling agents; nitro coupling agents such as N,N'-bis(2-methyl-2-nitropropyl)-1,6-diaminohexane (Sumifine 1162, from Sumitomo Chemical Co., Japan); and mixtures of any of the foregoing. The coupling agents may be provided as a mixture with a suitable carrier, for example X50-S, a mixture of Si-69 and N330 carbon black, available from Degussa AG.

The silica coated carbon blacks incorporated in the elastomeric compound of the present invention may be oxidized and/or combined with a coupling agent. Suitable oxidizing agents include, but are not limited to, nitric acid and similar compounds. Coupling agents include, but are not limited to, any of the coupling agents set forth above.

The partially coated embodiments of the present invention may further have an organic group attached. One process for attaching an organic group to the carbon black involves the reaction of at least one diazonium salt with a carbon black in the absence of an externally applied current sufficient to reduce the diazonium salt. That is, the reaction between the diazonium salt and the carbon black proceeds without an external source of electrons sufficient to reduce the diazonium salt. Mixtures of different diazonium salts may be used. This process can be carried out under a variety of reaction conditions and in any type of reaction medium, including both protic and aprotic solvent systems or slurries.

In another process, at least one diazonium salt reacts with a carbon black in a protic reaction medium. Mixtures of different diazonium salts may be used. This process can also be carried out under a variety of reaction conditions.

Preferably, in both processes, the diazonium salt is formed in situ. If desired, in either process, the carbon black product can be isolated and dried by means known in the art. Furthermore, the resultant carbon black product can be treated to remove impurities by known techniques. The various preferred embodiments of these processes are discussed below.

The processes can be carried out under a wide variety of conditions and in general are not limited by any particular condition. The reaction conditions must be such that the particular diazonium salt is sufficiently stable to allow it to react with the carbon black. Thus, the processes can be carried out under reaction conditions where the diazonium salt is short lived. The reaction between the diazonium salt and the carbon black occurs, for example, over a wide range of pH and temperature. The processes can be carried out at acidic, neutral, and basic pH. Preferably, the pH ranges from about 1 to 9. The reaction temperature may preferably range from 0° C. to 100° C.

Diazonium salts, as known in the art, may be formed for example by the reaction of primary amines with aqueous solutions of nitrous acid. A general discussion of diazonium salts and methods for their preparation is found in Morrison and Boyd, *Organic Chemistry,* 5th Ed., pp. 973–983, (Allyn and Bacon, Inc. 1987) and March, *Advanced Organic Chemistry: Reactions, Mechanisms, and Structures,* 4th Ed., (Wiley, 1992). According to this invention, a diazonium salt is an organic compound having one or more diazonium groups.

The diazonium salt may be prepared prior to reaction with the silica coated carbon black or, more preferably, generated in situ using techniques known in the art. In situ generation also allows the use of unstable diazonium salts such as alkyl diazonium salts and avoids unnecessary handling or manipulation of the diazonium salt. In particularly preferred processes, both the nitrous acid and the diazonium salt are generated in situ.

A diazonium salt, as is known in the art, may be generated by reacting a primary amine, a nitrite and an acid. The nitrite may be any metal nitrite, preferably lithium nitrite, sodium nitrite, potassium nitrite, or zinc nitrite, or any organic nitrite such as for example isoamylnitrite or ethyinitrite. The acid may be any acid, inorganic or organic, which is effective in the generation of the diazonium salt. Preferred acids include nitric acid, $HNO_3$, hydrochloric acid, HCl, and sulfuric acid, $H_2SO_4$.

The diazonium salt may also be generated by reacting the primary amine with an aqueous solution of nitrogen dioxide. The aqueous solution of nitrogen dioxide, $NO_2/H_2O$, provides the nitrous acid needed to generate the diazonium salt.

Generating the diazonium salt in the presence of excess HCl may be less preferred than other alternatives because HCl is corrosive to stainless steel. Generation of the diazonium salt with $NO_2/H_2O$ has the additional advantage of being less corrosive to stainless steel or other metals commonly used for reaction vessels. Generation using $H_2SO_4/NaNO_2$ or $HNO_3/NaNO_2$ are also relatively non-corrosive.

In general, generating a diazonium salt from a primary amine, a nitrite, and an acid requires two equivalents of acid based on the amount of amine used. In an in situ process, the diazonium salt can be generated using one equivalent of the acid. When the primary amine contains a strong acid group, adding a separate acid may not be necessary. The acid group or groups of the primary amine can supply one or both of the needed equivalents of acid. When the primary amine contains a strong acid group, preferably either no additional acid or up to one equivalent of additional acid is added to a process of the invention to generate the diazonium salt in situ. A slight excess of additional acid may be used. One example of such a primary amine is para-aminobenzenesulfonic acid (sulfanilic acid).

In general, diazonium salts are thermally unstable. They are typically prepared in solution at low temperatures, such as 0–5° C., and used without isolation of the salt. Heating solutions of some diazonium salts may liberate nitrogen and form either the corresponding alcohols in acidic media or the organic free radicals in basic media.

However, the diazonium salt need only be sufficiently stable to allow reaction with the carbon black. Thus, the processes can be carried out with some diazonium salts otherwise considered to be unstable and subject to decomposition. Some decomposition processes may compete with the reaction between the carbon black and the diazonium salt and may reduce the total number of organic groups attached to the carbon black. Further, the reaction may be carried out at elevated temperatures where many diazonium salts may be susceptible to decomposition. Elevated temperatures may also advantageously increase the solubility of the diazonium salt in the reaction medium and improve its handling during the process. However, elevated temperatures may result in some loss of the diazonium salt due to other decomposition processes.

Reagents can be added to form the diazonium salt in situ, to a suspension of carbon black in the reaction medium, for example, water. Thus, a carbon black suspension to be used may already contain one or more reagents to generate the diazonium salt and the process accomplished by adding the remaining reagents.

Reactions to form a diazonium salt are compatible with a large variety of functional groups commonly found on organic compounds. Thus, only the availability of a diazonium salt for reaction with a carbon black limits the processes of the invention.

The processes can be carried out in any reaction medium which allows the reaction between the diazonium salt and the carbon black to proceed. Preferably, the reaction medium is a solvent-based system. The solvent may be a protic solvent, an aprotic solvent, or a mixture of solvents. Protic solvents are solvents, like water or methanol, containing a hydrogen attached to an oxygen or nitrogen and thus are sufficiently acidic to form hydrogen bonds. Aprotic solvents are solvents which do not contain an acidic hydrogen as defined above. Aprotic solvents include, for example, solvents such as hexanes, tetrahydrofuran (THF), acetonitrile, and benzonitrile. For a discussion of protic and aprotic solvents see Morrison and Boyd, *Organic Chemistry*, 5th Ed., pp. 228–231, (Allyn and Bacon, Inc. 1987).

The processes are preferably carried out in a protic reaction medium, that is, in a protic solvent alone or a mixture of solvents which contains at least one protic solvent. Preferred protic media include, but are not limited to water, aqueous media containing water and other solvents, alcohols, and any media containing an alcohol, or mixtures of such media.

The reaction between a diazonium salt and a carbon black can take place with any type of carbon black, for example, in fluffy or pelleted form. In one embodiment designed to reduce production costs, the reaction occurs during a process for forming carbon black pellets. For example, a carbon black product can be prepared in a dry drum by spraying a solution or slurry of a diazonium salt onto a carbon black. Alternatively, the carbon black product can be prepared by pelletizing a carbon black in the presence of a solvent system, such as water, containing the diazonium salt or the reagents to generate the diazonium salt in situ. Aqueous solvent systems are preferred.

In general, the processes produce inorganic by-products, such as salts. In some end uses, such as those discussed below, these by-products may be undesirable. Several possible ways to produce a carbon black product without unwanted inorganic by-products or salts are as follows:

First, the diazonium salt can be purified before use by removing the unwanted inorganic by-product using means known in the art. Second, the diazonium salt can be generated with the use of an organic nitrite as the diazotization agent yielding the corresponding alcohol rather than an inorganic salt. Third, when the diazonium salt is generated from an amine having an acid group and aqueous $NO_2$, no inorganic salts are formed. Other ways may be known to those of skill in the art.

In addition to the inorganic by-products, a process may also produce organic by-products. They can be removed, for example, by extraction with organic solvents. Other ways of obtaining products without unwanted organic by-products may be known to those of skill in the art, and include washing or removal of ions by reverse osmosis.

The reaction between a diazonium salt and a silica coated carbon black forms a silica coated carbon black having an organic group attached to the carbon black. The diazonium salt may contain the organic group to be attached to the silica coated carbon black. It may be possible to produce the carbon black products by other means known to those skilled in the art.

The organic group may be an aliphatic group, a cyclic organic group, or an organic compound having an aliphatic portion and a cyclic portion. As discussed above, the diazonium salt employed can be derived from a primary amine having one of these groups and being capable of forming, even transiently, a diazonium salt. The organic group may be substituted or unsubstituted, branched or unbranched. Aliphatic groups include, for example, groups derived from alkanes, alkenes, alcohols, ethers, aldehydes, ketones, carboxylic acids, and carbohydrates. Cyclic organic groups include, but are not limited to, alicyclic hydrocarbon groups (for example, cycloalkyls, cycloalkenyls), heterocyclic hydrocarbon groups (for example, pyrrolidinyl, pyrrolinyl, piperidinyl, morpholinyl, and the like), aryl groups (for example, phenyl, naphthyl, anthracenyl, and the like), and heteroaryl groups (imidazolyl, pyrazolyl, pyridinyl, thienyl, thiazolyl, furyl, indolyl, and the like). As the steric hinderance of a substituted organic group increases, the number of organic groups attached to the carbon black from the reaction between the diazonium salt and the carbon black may be diminished.

When the organic group is substituted, it may contain any functional group compatible with the formation of a diazonium salt. Preferred functional groups include, but are not limited to, R, OR, COR, COOR, OCOR, carboxylate salts such as COOLi, COONa, COOK, COO$^-$NR$_4^+$, halogen, CN, NR$_2$, SO$_3$H, sulfonate salts such as SO$_3$Li, SO$_3$Na, SO$_3$K, SO$_3^-$NR$_4^+$, OSO$_3$H, OSO$_3^-$ salts, NR(COR), CONR$_2$, NO$_2$, PO$_3$H$_2$, phosphonate salts such as PO$_3$HNa and PO$_3$Na$_2$, phosphate salts such as OPO$_3$HNa and OPO$_3$Na$_2$, N=NR, NR$_3^+$X$^-$, PR$_3^+$X$^-$, S$_k$R, SSO$_3$H, SSO$_3^-$ salts, SO$_2$NRR', SO$_2$SR, SNRR', SNQ, SO$_2$NQ, CO$_2$NQ, S-(1,4-piperazinediyl)-SR, 2-(1,3-dithianyl) 2-(1,3-dithiolanyl), SOR, and SO$_2$R. R and R', which can be the same or different, are independently hydrogen, branched or unbranched C$_1$–C$_{20}$ substituted or unsubstituted, saturated or unsaturated hydrocarbon, e.g., alkyl, alkenyl, alkynyl, substituted or unsubstituted aryl, substituted or unsubstituted heteroaryl, substituted or unsubstituted alkylaryl, or substituted or unsubstituted arylalkyl. The integer k ranges from 1–8 and preferably from 2–4. The anion X$^-$ is a halide or an anion derived from a mineral or organic acid. Q is (CH$_2$)$_w$, (CH$_2$)$_x$O(CH$_2$)$_z$, (CH$_2$)$_x$NR(CH$_2$)$_z$, or (CH$_2$)$_x$S(CH$_2$)$_z$, where w is an integer from 2 to 6 and x and z are integers from 1 to 6.

A preferred organic group is an aromatic group of the formula A$_y$Ar—, which corresponds to a primary amine of the formula A$_y$ArNH$_2$. In this formula, the variables have the following meanings: Ar is an aromatic radical such as an aryl or heteroaryl group. Preferably, Ar is selected from the group consisting of phenyl, naphthyl, anthracenyl, phenanthrenyl, biphenyl, pyridinyl, benzothiadiazolyl, and benzothiazolyl; A is a substituent on the aromatic radical independently selected from a preferred functional group described above or A is a linear, branched or cyclic hydrocarbon radical (preferably containing 1 to 20 carbon atoms), unsubstituted or substituted with one or more of those functional groups; and y is an integer from 1 to the total number of —CH radicals in the aromatic radical. For instance, y is an integer from 1 to 5 when Ar is phenyl, 1 to 7 when Ar is naphthyl, 1 to 9 when Ar is anthracenyl, phenanthrenyl, or biphenyl, or 1 to 4 when Ar is pyridinyl. In the above formula, specific examples of R and R' are NH$_2$—C$_6$H$_4$—, CH$_2$CH$_2$—C$_6$H$_4$—NH$_2$, CH$_2$—C$_6$H$_4$—NH$_2$, and C$_6$H$_5$.

Another preferred set of organic groups which may be attached to a carbon black are organic groups substituted with an ionic or an ionizable group as a functional group. An ionizable group is one which is capable of forming an ionic group in the medium of use. The ionic group may be an anionic group or a cationic group and the ionizable group may form an anion or a cation.

Ionizable functional groups forming anions include, for example, acidic groups or salts of acidic groups. The organic groups, therefore, include groups derived from organic acids. Preferably, when it contains an ionizable group forming an anion, such an organic group has a) an aromatic group and b) at least one acidic group having a pKa of less than 11, or at least one salt of an acidic group having a pKa of less than 11, or a mixture of at least one acidic group having a pKa of less than 11 and at least one salt of an acidic group having a pKa of less than 11. The pKa of the acidic group refers to the pKa of the organic group as a whole, not just the acidic substituent. More preferably, the pKa is less than 10 and most preferably less than 9. Preferably, the aromatic group of the organic group is directly attached to the carbon black. The aromatic group may be further substituted or unsubstituted, for example, with alkyl groups. More preferably, the organic group is a phenyl or a naphthyl group and the acidic group is a sulfonic acid group, a sulfinic acid group, a phosphonic acid group, or a carboxylic acid group. Examples of these acidic groups and their salts are discussed above. Most preferably, the organic group is a substituted or unsubstituted sulfophenyl group or a salt thereof; a substituted or unsubstituted (polysulfo)phenyl group or a salt thereof; a substituted or unsubstituted sulfonaphthyl group or a salt thereof; or a substituted or unsubstituted (polysulfo) naphthyl group or a salt thereof. A preferred substituted sulfophenyl group is hydroxysulfophenyl group or a salt thereof.

Specific organic groups having an ionizable functional group forming an anion (and their corresponding primary amines) are p-sulfophenyl (p-sulfanilic acid), 4-hydroxy-3-sulfophenyl (2-hydroxy-5-amino-benzenesulfonic acid), and 2-sulfoethyl (2-aminoethanesulfonic acid). Other organic groups having ionizable functional groups forming anions may also be used.

Amines represent examples of ionizable functional groups that form cationic groups. For example, amines may be protonated to form ammonium groups in acidic media. Preferably, an organic group having an amine substituent has a pKb of less than 5. Quaternary ammonium groups (—NR$_3^+$) and quaternary phosphonium groups (—PR$_3^+$) also represent examples of cationic groups. Preferably, the organic group contains an aromatic group such as a phenyl or a naphthyl group and a quaternary ammonium or a quaternary phosphonium group. The aromatic group is preferably directly attached to the carbon black. Quaternized cyclic amines, and even quaternized aromatic amines, can also be used as the organic group. Thus, N-substituted pyridinium compounds, such as N-methyl-pyridyl, can be used in this regard. Examples of organic groups include, but are not limited to, (C$_5$H$_4$N)C$_2$H$_5^+$, C$_6$H$_4$(NC$_5$H$_5$)$^+$, C$_6$H$_4$COCH$_2$N(CH$_3$)$_3^+$, C$_6$H$_4$COCH$_2$(NC$_5$H$_5$)$^+$, (C$_5$H$_4$N) CH$_3^+$, and C$_6$H$_4$CH$_2$N(CH$_3$)$_3^+$.

An advantage of the carbon black products having an attached organic group substituted with an ionic or an ionizable group is that the carbon black product may have increased water dispersibility relative to the corresponding untreated carbon black. Water dispersibility of a carbon black product increases with the number of organic groups attached to the carbon black having an ionizable group or the number of ionizable groups attached to a given organic group. Thus, increasing the number of ionizable groups associated with the carbon black product should increase its water dispersibility and permits control of the water dispersibility to a desired level. It can be noted that the water dispersibility of a carbon black product containing an amine as the organic group attached to the carbon black may be increased by acidifying the aqueous medium.

Because the water dispersibility of the carbon black products depends to some extent on charge stabilization, it is preferable that the ionic strength of the aqueous medium be less than 0.1 molar. More preferably, the ionic strength is less than 0.01 molar.

When such a water dispersible carbon black product is prepared, it is preferred that the ionic or ionizable groups be ionized in the reaction medium. The resulting product solution or slurry may be used as is or diluted prior to use. Alternatively, the carbon black product may be dried by techniques used for conventional carbon blacks. These techniques include, but are not limited to, drying in ovens and rotary kilns. Overdrying, however, may cause a loss in the degree of water dispersibility.

In addition to their water dispersibility, carbon black having an organic group substituted with an ionic or an ionizable group may be dispersible in polar organic solvents such as dimethylsulfoxide (DMSO), and formamide. In alcohols such as methanol or ethanol, use of complexing agents such as crown ethers increases the dispersibility of carbon black products having an organic group containing a metal salt of an acidic group.

Aromatic sulfides encompass another group of preferred organic groups. Carbon black products having aromatic sulfide groups are particularly useful in rubber compositions. These aromatic sulfides can be represented by the formulas $Ar(CH_2)_qS_k(CH_2)_rAr'$ or $A-(CH_2)_qS_k(CH_2)_rAr''$ wherein Ar and Ar' are independently substituted or unsubstituted arylene or heteroarylene groups, Ar" is an aryl or heteroaryl group, k is 1 to 8 and q and r are 0–4. Substituted aryl groups would include substituted alkylaryl groups. Preferred arylene groups include phenylene groups, particularly p-phenylene groups, or benzothiazolylene groups. Preferred aryl groups include phenyl, naphthyl and benzothiazolyl. The number of sulfurs present, defined by k preferably ranges from 2 to 4. Preferred carbon blacks are those having an attached aromatic sulfide organic group of the formula $-(C_6H_4)-S_k-(C_6H_4)-$, where k is an integer from 1 to 8, and more preferably where k ranges from 2 to 4. Particularly preferred aromatic sulfide groups are bis-para-$(C_6H_4)-S_2-(C_6H_4)-$ and para-$(C_6H_4)-S_2-(C_6H_5)$. The diazonium salts of these aromatic sulfide groups may be conveniently prepared from their corresponding primary amines, $H_2N-Ar-S_k-Ar'-NH_2$ or $H_2N-Ar-S_k-Ar''$. Preferred groups include dithiodi-4,1-phenylene, tetrathiodi-4,1-phenylene, phenyldithiophenylene, dithiodi-4,1-(3-chlorophenylene), $-(4-C_6H_4)-S-S-(2-C_7H_4NS)$, $-(4-C_6H_4)-S-S-(4-C_6H_4)-OH$, $-6-(2-C_7H_3NS)-SH$, $-(4-C_6H_4)-CH_2CH_2-S-S-CH_2CH_2-(4-C_6H_4)-$, $-(4-C_6H_4)-CH_2CH_2-S-S-S-CH_2CH_2-(4-C_6H_4)-$, $-(2-C_6H_4)-S-S-(2-C_6H_4)-$, $-(3-C_6H_4)-S-S-(3-C_6H_4)-$, $-6-(C_6H_3N_2S)$, $-6-(2-C_7H_3NS)-S-NRR'$ where RR' is $-CH_2CH_2OCH_2CH_2-$, $-(4-C_6H_4)-S-S-S-S-(4-C_6H_4)-$, $-(4-C_6H_4)-CH=CH_2$, $-(4-C_6H_4)-S-SO_3H$, $-(4-C_6H_4)-SO_2NH-(4-C_6H_4)-S-S-(4-C_6H_4)-NHSO_2-(4-C_6H_4)-$, $-6-(2-C_7H_3NS)-S-S-2-(6-C_7H_3NS)-$, $-(4-C_6H_4)-S-CH_2-(4-C_6H_4)-$, $-(4-C_6H_4)-SO_2-S-(4-C_6H_4)-$, $-(4-C_6H_4)-CH_2-S-CH_2-(4-C_6H_4)-$, $-(3-C_6H_4)-CH_2-S-CH_2-(3-C_6H_4)-$, $-(4-C_6H_4)-CH_2-S-S-CH_2-(4-C_6H_4)-$, $-(3-C_6H_4)-CH_2-S-S-CH_2-(3-C_6H_4)-$, $-(4-C_6H_4)-S-NRR'$ where RR' is $-CH_2CH_2OCH_2CH_2-$, $-(4-C_6H_4)-SO_2NH-CH_2CH_2-S-S-CH_2CH_2-NHSO_2-(4-C_6H_4)-$, $-(4-C_6H_4)-2-(1,3-dithianyl)$, and $-(4-C_6H_4)-S-(1,4-piperizinediyl)-S-(4-C_6H_4)-$.

Another preferred set of organic groups which may be attached to the carbon black are organic groups having an aminophenyl, such as $(C_6H_4)-NH_2$, $(C_6H_4)-CH_2-(C_6H_4)-NH_2$, $(C_6H_4)-SO_2-(C_6H_4)-NH_2$. Preferred organic groups also include aromatic sulfides, represented by the formulas $Ar-S_n-Ar'$ or $Ar-S_n-Ar''$, wherein Ar and Ar' are independently arylene groups, Ar" is an aryl, and n is 1 to 8. Methods for attaching such organic groups to carbon black are discussed in U.S. patent applications Ser. Nos. 08/356,660, 08/572,525, and 08/356,459, the disclosures of which are fully incorporated by reference herein.

In addition, a mixture of silica coated carbon black and a modified carbon black having at least one attached organic group may be used. Furthermore, it is within the bounds of this application to also use a mixture of silica and silica coated carbon black. Also, any combination of additional components with the silica coated carbon black may be used, such as one of the following:

a) silica coated carbon black with an attached organic group optionally treated with silane coupling agents;

b) modified carbon black having an attached organic group;

c) silica;

d) modified silica, for example, having an attached organic group; and/or e) carbon black.

Examples of silica include, but are not limited to, silica, precipitated silica, amorphous silica, vitreous silica, fumed silica, fused silica, silicates (e.g., aluminosilicates), and other Si-containing fillers such as clay, talc, wollastonite, and the like. Silicas are commercially available from such sources as Cabot Corporation under the Cab-O-Sil® tradename, PPG industries under the Hi—Sil and Ceptane tradenames, Rhone-Poulence under the Zeosil tradename; and Degussa AG under the Ultrasil and Coupsil tradenames.

Any suitable elastomer may be compounded with the silica coated carbon blacks to provide the elastomeric compounds of the present invention. Such elastomers include, but are not limited to, homo- or co-polymers of 1,3 butadiene, styrene, isoprene, isobutylene, 2,3-dimethyl-1,3-butadiene, acrylonitrile, ethylene, and propylene, preferably wherein the glass transition temperature (Tg) as measured by Differential Scanning Calorimetry (DSC) ranges from about −120° C. to about 0° C. Examples include, but are not limited to, SBR, natural rubber and its derivatives such as chlorinated rubber, polybutadiene, polyisoprene, poly (styrene-co-butadiene), and blends of any of the foregoing. SBRs include, but are not limited to, solution SBR, functional solution SBR, emulsion SBR, and combinations of any of the foregoing.

The silica coated carbon black of the invention may also be used with synthetic rubbers such as: copolymers of from about 10 to about 70 percent by weight of styrene and from about 90 to about 30 percent by weight of butadiene such as copolymer of 19 parts styrene and 81 parts butadiene, a copolymer of 30 parts styrene and 70 parts butadiene, a copolymer of 43 parts styrene and 57 parts butadiene and a copolymer of 50 parts styrene and 50 parts butadiene; polymers and copolymers of conjugated dienes such as polybutadiene, polyisoprene, polychloroprene, and the like, and copolymers of such conjugated dienes with an ethylenic group-containing monomer copolymerizable therewith such as styrene, methyl styrene, chlorostyrene, acrylonitrile, 2-vinyl-pyridine, 5-methyl 2-vinylpyridine, 5-ethyl-2-vinylpyridine, 2-methyl-5-vinylpyridine, alkyl-substituted acrylates, vinyl ketone, methyl isopropenyl ketone, methyl vinyl either, alphamethylene carboxylic acids and the esters and amides thereof such as acrylic acid and dialkylacrylic acid amide; also suitable for use herein are copolymers of ethylene and other high alpha olefins such as propylene, butene-1 and pentene-1.

Elastomeric compositions also include vulcanized compositions (VR), thermoplastic vulcanizates (TPV), thermoplastic elastomers (TPE), and thermoplastic polyolefins (TPO). TPV, TPE, and TPO materials are further classified by their ability to be extruded and molded several times without loss of performance characteristics.

In making the elastomeric compositions, one or more curing agents such as, for example, sulfur, sulfur donors, activators, accelerators, peroxides, and other systems used to effect vulcanization of the elastomer composition may be used.

The elastomeric compositions of the present invention may contain an elastomer, curing agents, reinforcing filler, a coupling agent, and, optionally, various processing aids, oil extenders, and antidegradents.

Formulation of the silica coated carbon blacks of the present invention with elastomers are contemplated to have advantages not realized when such elastomers are formulated with conventional carbon blacks. Set forth below in Table 1 is a list of certain of the elastomers which are particularly useful for industrial rubber applications; and preferred loading ratios with the silica coated carbon blacks of the present invention, designated as parts of carbon black per hundred parts of elastomer (PHR); contemplated benefits obtained by such composition compared to the same composition employing a conventional carbon black; and useful industrial applications for each composition corresponding, where applicable, to the contemplated benefit obtained with such composition. In addition to EPDM and peroxide cured elastomers, advantages for this silica coated carbon black would also be expected in elastomers containing elements other than carbon and hydrogen. Examples of elastomers containing non-hydrogen groups would include but not be limited to NBR (acrylonitrile-butadiene rubber), XNBR (carboxylic-acrylonitrile-butadiene rubber), HNBR (hydrogenated-acrylonitrile-butadiene rubber), CR (chloroprene rubber), ECO (ethylene oxide-chloromethyl oxirane), GPO (polypropylene oxide-allyl glycidyl ether), PPO (polypropylene oxide), CSM (chloro-sulfonyl-polyethylene), CM (chloro-polyethylene), BIIR (bromo-isobutene-isoprene rubber), CIIR (chloroisobutene-isoprene rubber), ACM (copolymers of ethyl or other acrylate and small amount of vulcanizable co-monomer), and AEM (copolymers of ethyl or other acrylate and ethylene).

The contemplated benefits obtained with the compositions set forth in Table 1 are characterized by expected properties compared to the same composition made with conventional (non-silica coated) carbon black. Evaluation of these properties for a given silica coated carbon black/elastomer composition is done by conducting comparative tests. Most of the properties set forth in Table 1 are determined by routine tests known to those skilled in the art. Other tests are briefly described below:

Hardness refers to Shore A Hardness, which is determined according to the procedure set forth in ASTM D-2240-86.

Resilience may be determined according to the procedure set forth in ASTM D1054, utilizing a ZWICK Rebound Resilience Tester, Model 5109, manufactured by Zwick of America, Inc., Post Office Box 997, East Windsor, Conn. 06088.

TABLE 1

| POLYMER | LOADING | BENEFITS UPON FORMING | FIELD OF APPLICATION |
|---|---|---|---|
| Ethylene Propylene Diene Monomer (EPDM) | 50–250 PHR 100–200 PHR | INCREASED UHF HEATING RATES | WEATHERSTRIP |
| | | INCREASED TEAR STRENGTH | WEATHERSTRIP |
| | | REDUCED IRIDESCENCE | WEATHERSTRIP |
| | | IMPROVED HEAT AGING RESISTANCE | HOSE |
| | | HIGHER ELECTRICAL RESISTIVITY | HOSE |
| | | INCREASED ELONGATION @ GIVEN HARDNESS | HOSE |
| | | LONGER FATIGUE LIFE | ENGINE MOUNTS |
| | | LOWER SPRING RATIO FOR A GIVEN TAN $\delta$ | ENGINE MOUNTS |
| | | IMPROVED RESILENCE | ENGINE MOUNTS |
| Poly-Chloroprene (NEOPRENE) | 10–150 phr 20–80 phr | LOWER SPRING RATIO FOR A GIVEN TAN $\delta$ | ENGINE MOUNTS |
| | | IMPROVED GLYCOL RESISTANCE | SEALS |
| | | IMPROVED RESILENCE | SEALS, HOSE |
| | | LOWER HEAT BUILD-UP | BELTS |
| Natural Rubber (NR) | 10–150 phr 20–80 phr | LOWER SPRING RATIO FOR A GIVEN TAN $\delta$ | ENGINE MOUNTS |
| | | HIGHER CUT/CHIP RESISTANCE | BELTS |
| Hydrogenated Nitrile Butadiene Rubber (HNBR) | 10–150 phr 20–80 phr | LOWER SPRING RATIO FOR A GIVEN TAN $\delta$ | ENGINE MOUNTS |
| | | INCREASED HIGH TEMP TEAR RESISTANCE | MOUNTS, SEALS |
| | | IMPROVED RESILIENCE | SEALS, HOSE |
| | | LOWER HEAT BUILD-UP | BELTS |
| Styrene Butadiene Rubber (SBR) | 10–150 phr | HIGHER CUT/CHIP RESISTANCE | BELTS |
| Ethylene Vinyl Acetate (EVA) | 10–150 phr | IMPROVED PHYSICAL PROPERTIES | HOSE |

The UHF microwave receptivity may be measured by a Dielecmeter (supplied by Total Elastomers in France). The UHF microwave receptivity is characterized by a coefficient, α, which is defined as $$\alpha = (150°\,C. - 80°\,C.)/(t_{150} - t_{80})\ [°\,C./s]$$

where $t_{150}$ and $t_{80}$ are the times needed for samples to reach 150° C. and 80° C. respectively. α is the heating rate between temperatures 80° and 150° C.

The electrical resistivity of the composition may be measured by painting samples 2 inches wide by 6 inches long by 0.085 inch thick with a half inch width of silver paint. The sample is then conditioned to produce a stable reading by cycling from room temperature to 100° C. and back to room temperature, followed by aging at 90° C. for 24 hours. The stabilized resistivity was measured at the end of the aging cycle, and once again after the sample was allowed to cool back to room temperature.

The resultant elastomeric compounds containing silica coated carbon black and optionally containing one or more coupling agents may be used for various elastomeric products such as treads for vehicle tires, industrial rubber products, seals, timing belts, power transmission belting, and other rubber goods. When utilized in tires, the elastomeric compounds may be used in the tread or in other components of the tire, for example, the carcass and sidewall.

Tread compounds produced with the present elastomeric compounds incorporating a silica coated carbon black but without a coupling agent, provide improved dynamic hysteresis characteristics. However, elastomeric compounds incorporating a partially coated carbon black and a coupling agent demonstrate further improved characteristics.

All patents, applications, test methods, and publications mentioned herein are incorporated by reference.

Many variations of the present invention will suggest themselves to those skilled in the art in light of the above detailed disclosure. For example, the compositions of the present invention may include other reinforcing agents, other fillers, oil extenders, antidegradants, and the like. All such modifications are within the full intended scope of the claims.

We claim:

1. An elastomeric compound comprising:
   an elastomer selected from the group consisting of ethylene propylene diene monomer rubber, poly chloroprene, natural rubber, hydrogenated nitrile butadiene rubber, nitrile butadiene rubber, chlorinated polyethylene, styrene butadiene rubber, butyl rubber, polyacrylic rubber, polyepichlorohydrin, ethylene vinyl acetate and blends of the foregoing; and
   a silica coated carbon black, and
   wherein at least a portion of said silica coated carbon black has an organic group attached thereto, and is optionally treated with a silane coupling agent.

2. The elastomeric compound of claim 1 wherein said silica coated carbon black is present in an amount of from between about 10 and 300 parts per hundred parts of said elastomer.

3. The elastomeric compound of claim 2 wherein said silica coated carbon black is present in an amount of from between about 100 and 200 parts per hundred parts of said elastomer.

4. The elastomeric compound of claim 1 wherein said silica coated carbon black is present in an amount of from between about 10 and 150 parts per hundred parts of said elastomer.

5. The elastomeric compound of claim 4 wherein said silica coated carbon black is present in an amount of from between about 20 and 80 parts per hundred parts of said elastomer.

6. An article of manufacture formed from the elastomeric compound of claim 1.

7. The article of claim 6 wherein said elastomeric compound is formed into weatherstripping.

8. The article of claim 6 wherein said elastomeric compound is formed into coolant hose.

9. The article of claim 6 wherein said elastomeric compound is formed into hydraulic hose.

10. The article of claim 6 wherein said elastomeric compound is formed into fuel hose.

11. The article of claim 6 wherein said elastomeric compound is formed into an engine mount.

12. The article of claim 6 wherein said elastomeric compound is formed into a bushing.

13. The article of claim 6 wherein said elastomeric compound is formed into a power belt.

14. The article of claim 6 wherein said elastomeric compound is formed into a conveyor belt.

15. The article of claim 6 wherein said elastomeric compound is formed into a power transmission belt.

16. The article of claim 6 wherein said elastomeric compound is formed into a seal.

17. The article of claim 6 wherein said elastomeric compound is formed into a gasket.

18. An elastomeric compound comprising an elastomer and a silica coated carbon black, wherein said carbon black is at least partially coated with silica, and
   wherein at least a portion of said silica coated carbon black has an organic group attached thereto, and is optionally treated with a silane coupling agent.

19. The elastomeric compound of claim 18, wherein said elastomer is selected from the group consisting of solution SBR, natural rubber, functional solution SBR, emulsion SBR, polybutadiene, polyisoprene, and blends of any of the foregoing.

20. The elastomeric compound of claim 18, wherein said silica coated carbon black contains between about 0.5% and about 10% silicon, by weight.

21. The elastomeric compound of claim 20, wherein said silica coated carbon black contains between about 2% and about 6% silicon, by weight.

22. The elastomeric compound of claim 18 further comprising a coupling agent.

23. The elastomeric compound of claim 22, wherein said coupling agent is selected from the group consisting of silane coupling agents, zirconate coupling agents, titanate coupling agents, nitro coupling agents, and mixtures of any of the foregoing.

24. The elastomeric compound of claim 23, wherein said coupling agent is selected from the group consisting of bis(3-triethoxysilylpropyl)tetrasulfane, 3-thiocyanatopropyl-triethoxy silane, γ-mercaptopropyl-trimethoxy silane, zirconium dineoalkanolatodi(3-mercapto) propionato-O, N,N'-bis(2-methyl-2-nitropropyl)-1,6-diaminohexane and mixtures of the foregoing.

25. A method for improving the hysteresis of an elastomeric compound comprising compounding an elastomeric compound as defined in claim 18, wherein said silica coated carbon black imparts to the elastomer higher loss tangent at low temperature and a lower loss tangent at high temperature, compared to an uncoated carbon black.

26. The elastomeric compound of claim 1, further comprising silica.

27. The elastomeric compound of claim 1, further comprising carbon black, silica, or combinations thereof.

28. The elastomeric compound of claim 18, wherein said organic group is Ar—$S_n$—Ar' or Ar—$S_n$—Ar", wherein Ar and Ar' are independently arylene groups, Ar" is an aryl, and n is 1 to 8.

29. The elastomeric compound of claim 1, further comprising a carbon black having an organic group attached thereto.

30. The elastomeric compound of claim 1, further comprising carbon black.

31. The elastomeric compound of claim 1, wherein said elastomeric composition further comprises a carbon black having an organic group attached thereto, silica, carbon black, or mixtures thereof.

32. A formulation for making an elastomeric composition, comprising an elastomer and a silica coated carbon black, wherein at least a portion of said silica coated carbon black has an organic group attached thereto, and is optionally treated with a silane coupling agent.

33. The formulation of claim 32, further comprising a coupling agent.

* * * * *